United States Patent [19]
Davidson et al.

[11] Patent Number: 5,169,597
[45] Date of Patent: Dec. 8, 1992

[54] BIOCOMPATIBLE LOW MODULUS TITANIUM ALLOY FOR MEDICAL IMPLANTS

[76] Inventors: James A. Davidson, 2573 Windy Oaks Rd., Germantown, Tenn. 38138; Paul Kovacs, 3227 S. Mendenhall Rd., Memphis, Tenn. 38115

[21] Appl. No.: 647,453
[22] Filed: Jan. 28, 1991

Related U.S. Application Data

[63] Continuation of Ser. No. 454,181, Dec. 21, 1989, abandoned.

[51] Int. Cl.⁵ ............................................ C22C 14/00
[52] U.S. Cl. .................................. 428/613; 148/421; 148/669; 148/316; 420/418; 420/417; 606/76; 606/78; 623/16; 428/408; 428/469; 428/636
[58] Field of Search ................ 420/417, 421; 148/421, 148/133; 606/78, 76

[56] References Cited

U.S. PATENT DOCUMENTS

| | | |
|---|---|---|
| 4,040,129 | 8/1977 | Steinemann et al. ............ 148/11.5 F |
| 4,170,990 | 10/1979 | Baumgart et al. ...................... 606/78 |
| 4,857,269 | 8/1989 | Wang et al. ............................ 420/417 |
| 4,902,359 | 2/1990 | Takeuchi et al. ..................... 148/133 |

FOREIGN PATENT DOCUMENTS 2703529  8/1978  Fed. Rep. of Germany .

OTHER PUBLICATIONS

Zwicker et al. Z. Metallkunde, 61 (1970) pp. 836-847.
Collins (ed) A Sourcebook of Titanium Alloy Superconductivity, Plenum, N.Y. 1983 pp. 342, 352, 357, 358, 366, 405-412, 418-419.
Albert et al. Z. Metallunde, 63 (1972) 126.

*Primary Examiner*—Upendra Roy
*Attorney, Agent, or Firm*—Pravel, Gambrell, Hewitt, Kimball & Krieger

[57] ABSTRACT

A biocompatible titanium alloy with low elastic modulus containing titanium, about 10-20 wt. % or 35 to about 50 wt. % niobium and up to 20 wt. % zirconium useful for fabricating of orthopedic implants. This invention relates generally to high strength, biocompatible alloys suitable for use as a material for a medical prosthetic implant and, in particular, a titanium alloy which has a relatively low modulus of elasticity (e.g. closer to that of bone than other typically-used metal alloys) and does not include any elements which have been shown or suggested as having short term or long term potential adverse effect from a standpoint or biocompatibility.

7 Claims, 3 Drawing Sheets

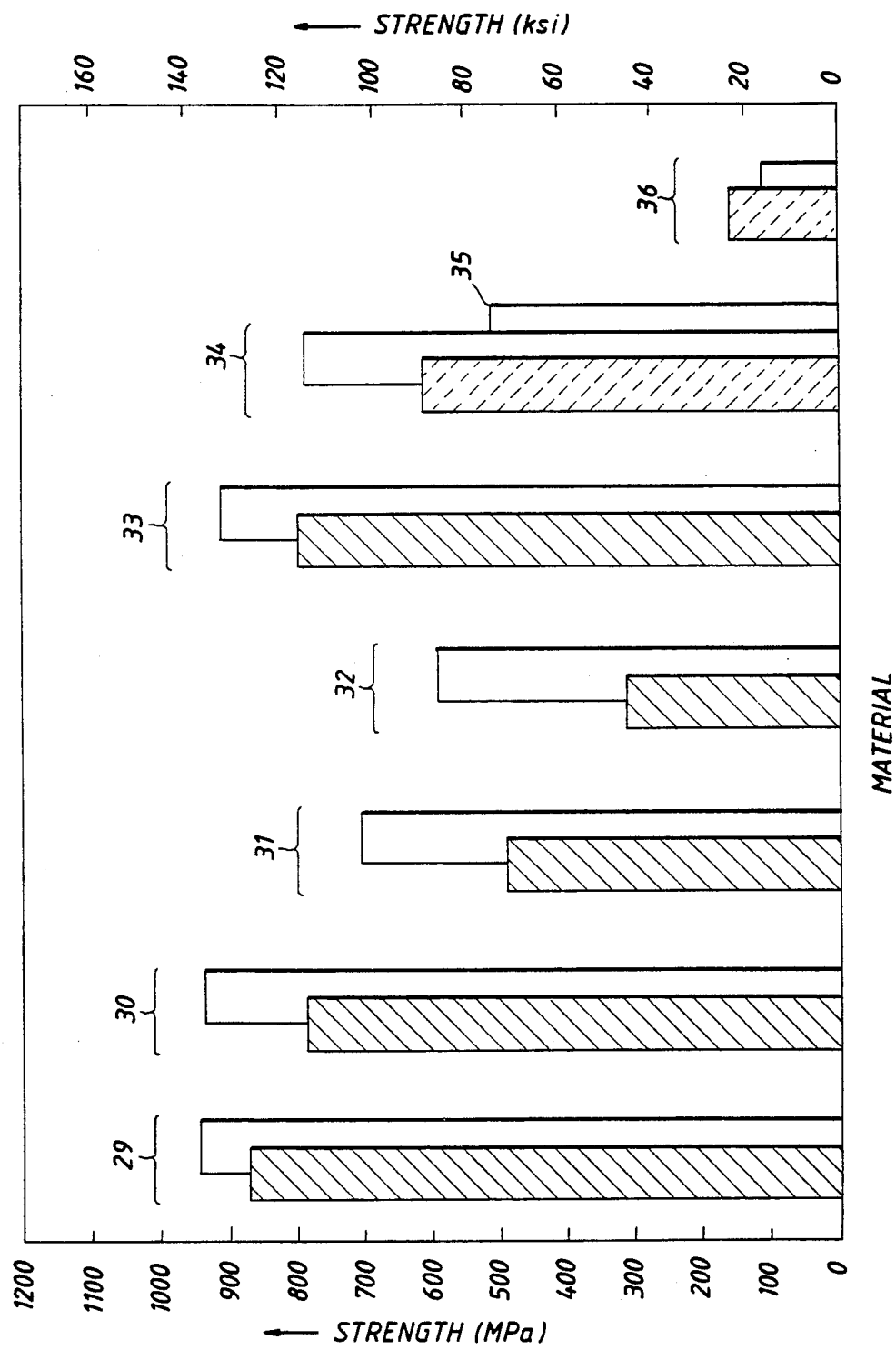

BIOCOMPATIBLE LOW MODULUS TITANIUM ALLOY FOR MEDICAL IMPLANTS

This is a continuation of application Ser. No. 07/454,181 filed Dec. 21, 1989, now abandoned.

BACKGROUND

1. Field of the Invention

This invention relates to high strength, biocompatible alloys suitable for use as a material for a medical prosthetic implant and, in particular, a titanium alloy which has a relatively low modulus of elasticity (e.g. closer to that of bone than other typically-used metal alloys) and does not include any elements which have been shown or suggested as having short term or long term potential adverse effect.

2. Background of the Invention

The most common materials used for load-bearing medical implants such as hip or bone prostheses are metallic alloys, ceramics and composites formed of biocompatible polymers and various reinforcing materials.

Polymers are typically used in implants such as intraocular lenses, facial bone remodeling and other non-load bearing applications. In order to use plastic materials in load-bearing applications, they are typically reinforced with a particulate or high modulus fibrous material, such as carbon fiber, to produce composites of acceptable strength capable of withstanding relatively great applied loads. Although composites are presently under consideration by many companies, their usefulness as an implant material lies in their relatively low elastic modulus compared to metal and ceramic implants, and their optimum design characteristics are still being explored.

Ceramic prostheses provide excellent biocompatibility, corrosion resistance (inertness) and high compression strength for load-bearing applications. However, ceramic prostheses are typically rigid (high elastic modulus), and unyielding under stress from loads applied during normal use, so that it cannot effectively transfer stresses to surrounding bone. Thus, bone decalcification which results in localized thinning (resorption) and weakening of the bone structure may occur.

Metals and metal alloys such as stainless steel, vitalium (cobalt alloy) and titanium have been used successfully. These materials have the requisite strength characteristics but typically have not been resilient or flexible enough to form an optimum implant material. Also, many alloys contain elements such as aluminum, vanadium, cobalt, nickel, molybdenum, and chromium which recent studies have suggested might have some long term adverse effects on human patients.

Many of the metal alloys typically used in prosthetic implants were developed for other applications such as Ti-6Al-4V in alloy in the aircraft industry. These alloys were later thought to be suitable for use as implant materials because they possess mechanical strength and appeared to have acceptable levels of biocompatibility. However, these metals typically have elastic moduli much higher than that of bone, for example, 316 stainless steel has an elastic modulus of about 200 GPa while that of cast heat-treated Co-Cr-Mo alloy is about 240 GPa. Of these, the alloy with the lowest elastic modulus is Ti-6Al-4V with an elastic modulus of about 120 GPa.

It has also been found that many of these metals will corrode to some extent in body fluids thereby releasing ions that might possibly be harmful over a prolonged period of time. It is now believed that the corrosive effects of body fluids is due both to chemical and electro-chemical processes, with corrosion products forming hen certain commonly-used metal alloys ionize from corrosion processes in the body. For example, aluminum metal ions have been associated with Alzheimer's disease and vanadium, cobalt, molybdenum, nickel and chromium are suspected of being toxic or carcinogenic.

It has been suggested that metals could be coated with a biocompatible plastic, ceramic or oxide to overcome the corrosion problem. However, coatings tend to wear off, especially on articulating bearing surfaces of total joints, and are susceptible to galling and separating from the metal substrate, exposing the metal to body fluids.

Generally, it is the industry practice to passivate the implant metal alloys. However, passivation produces only thin amorphous, poorly attached protective oxide films have not proved totally effective in eliminating the formation of corrosion products in the body, particularly in situations where fretting occurs in the body.

Titanium alloys offer advantages over the stainless steels because of their lower susceptibility to corrosion in the body coupled with their high strength and relatively low modulus of elasticity. Upon cooling, the currently used Ti-6Al-4V alloy transforms from a $\beta$-structure to an $\alpha$- plus $\beta$-structure at about 1000° C. This transition can be shifted to a lower temperature by the addition of one or more suitable $\beta$-phase stabilizers such as molybdenum, zirconium, niobium, vanadium, tantalum, cobalt, chromium, iron, manganese and nickel.

Some efforts have been directed toward the development of alloys that eliminate harmful metals. For example, U.S. Pat. No. 4,040,129 to Steinemann et al. is directed to an alloy which includes titanium or zirconium as one component and, as a second component, any one or more of: nickel, tantalum, chromium, molybdenum or aluminum, but does not recognize or suggest any advantages from having a relatively low elastic modulus, or advantages or disadvantages associated with high temperature sintering treatments (at about 1250° C.), commonly employed to attach porous metal coatings into which bone can grow to stabilize noncemented, press-fit devices into the skeletal structure. Steinemann also indicates that the ultimate tensile strength should be greater than about 979 MPa (142 ksi) with a minimum tensile elongation of 10%.

Although Steinemann provides that copper, cobalt, nickel, vanadium and tin should be excluded, apart from their presence as unavoidable impurities, the patent indicates that it is permissible to have any or all of chromium, molybdenum and aluminum, which are all believed to have potential long-term adverse effects, present in the alloy as long as their combined weight does not exceed 20% of the total weight of the alloy.

U.S. Pat. No. 4,857,269 to Wang et al. is not a statutory bar and its citation is not an admission that its teachings are applicable prior art. This patent relates to a titanium alloy for a prosthetic implant said to have high strength and a low modulus. The titanium alloy contains up to 24 wt. % of at least one isomorphous beta stabilizer from the group molybdenum, tantalum, zirconium and niobium; up to 3 wt. % of at least one eutectoid beta stabilizer from the group iron, manganese, chromium, cobalt or nickel; and optionally up to 3 wt. % of a metallic $\alpha$-stabilizer from the group aluminum and lanthanum. Incidental impurities up to 0.05% carbon, 0.30% oxygen, 0.02% nitrogen, and up to 0.02% of the eutectoid former hydrogen are also included. Although there is some discussion of having an elastic modulus (e.g., Young's modulus) around 85 GPa, the only examples of a low modulus (66.9–77.9 GPa) all contain 11.5 wt. % Mo which is a potentially toxic element and undesirable for optimizing biocompatibility.

Other currently used metal alloys have similar drawbacks. For example, the commonly used Ti-6Al-4V alloy, with appropriate heat treatment, offers some degree of biocompatibility but has an elastic modulus of about 120 GPa. Although this elastic modulus is lower than other alloys and accordingly offers better load transfer to the surrounding bone, this modulus is still significantly greater than desired. Moreover, the alloy contains aluminum and also vanadium, which is now suspected to be a toxic or carcinogenic material when present in sufficient quantity.

Commercially available PROTOSUL 100 (Sulzer Bros. Ltd.) is a Ti-6Al-7Nb alloy which intentionally avoids the potentially adverse effects of vanadium toxicity by substituting niobium. However, the alloy still contains aluminum and has an elastic modulus of about 110 GPa ($15.9 \times 10^6$ psi) in heat-treated condition, and with a tensile strength of about 1060 MPa.

With orthopedic prostheses being implanted in younger people and remaining in the human body for longer periods of time, there is a need for an implant material with requisite strength and flexibility requirements, which does not contain elements which are suspected as having long-term harmful effects on the human body.

BRIEF DESCRIPTION OF THE DRAWINGS

FIG. 3 is a bar graph comparing the mechanical properties of an invention alloy with other materials and bone.

SUMMARY OF THE INVENTION

The invention is a material useful in the manufacture of orthopedic implants, which possess the characteristics of relatively high strength, exceptionally low modulus of elasticity, and is free from any potentially toxic elements. The alloy contains about 74 wt. % titanium, and about 13 wt. % each of zirconium and niobium. Other elements are not deliberately added, but may be present in trace amounts to the extent that they were present as unavoidable impurities in the metals used to produce the alloy. Other non-toxic filler materials such as tantalum, which could be used to stabilize the β-phase, but not affect the low modulus, i.e. maintain it less than about 85 GPa, could also be added. The exclusion of elements beside titanium, zirconium and niobium or tantalum results in an alloy which does not contain known toxins or carcinogens or elements that are known or suspected of inducing diseases or adverse tissue response in the long term.

The inventive titanium alloy is rapidly cooled from above the β-transus and aged to provide adequate strength. Further, the inventive alloy has a low modulus of elasticity, even after high-temperature sintering to attach porous-coatings, of about 62–75 GPa. This compares favorably with the elastic modulus of fiber reinforced polymer composites, which are typically in the range 60–70 GPa for strength adequate for long-term in-vivo loading, and is a significant improvement over Ti-6Al-4V which has a modulus of elasticity of about 120 GPa.

Figure 2:
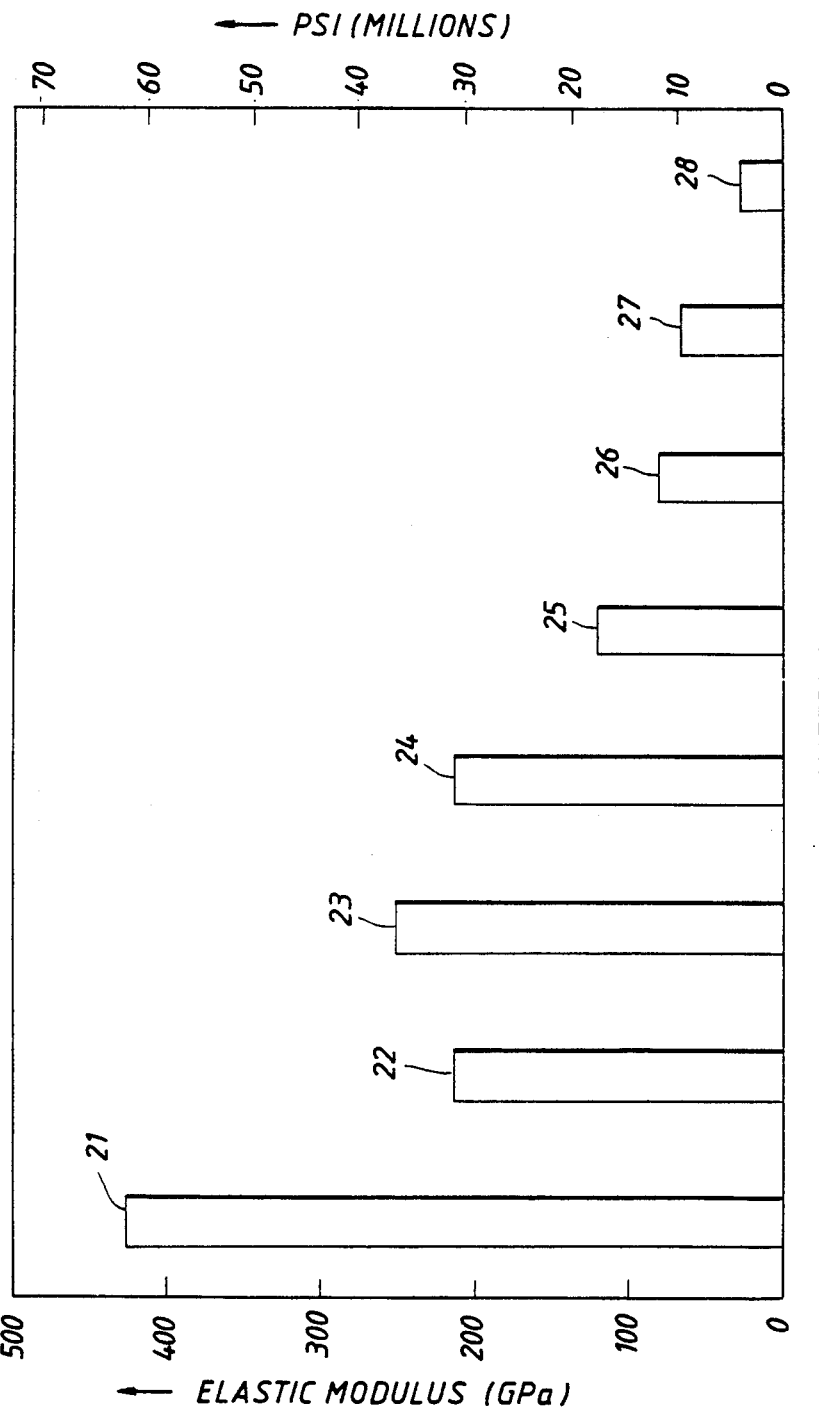
FIG. 2 is a bar graph comparing the mechanical properties of an invention alloy with other materials and bone.

A comparison of the mechanical properties of the invention Ti-13Zr-13Nb alloy with other implant materials is shown in FIG. 2 where the elastic modulus of alumina is represented by the bar marked 21, zirconia by 22, cobalt-chrome-molybdenum by 23, 316 SS by 24, Ti-6Al-4V by 25, the invention Ti-13Zr-13Nb by 26, a composite of polyetheretherketone and carbon fiber by 27 and cortical bone by 28. Further, the mechanical properties of the invention alloy implants are compared with other alloys in FIG. 3 where Ti-13Zr-13Nb is represented by 29, 316 SS (30% CW) by 30, cast cobalt-chrome-molybdenum by 31, 316 SS by 32, Ti-13Zr-13Nb by 33, a composite of polyetheretherketone and carbon by 34, a carbon polysulfone composite by 35, and cortical bone by 36.

In certain applications it may still be desirable to coat the alloy surface with wear-resistant coatings such as amorphous diamond-like carbon coatings, zirconium dioxide coatings, titanium nitrides, carbides, or the like for protection against potential micro-fretting, such as might occur on the bearing surfaces of implant prostheses.

Figure 1:
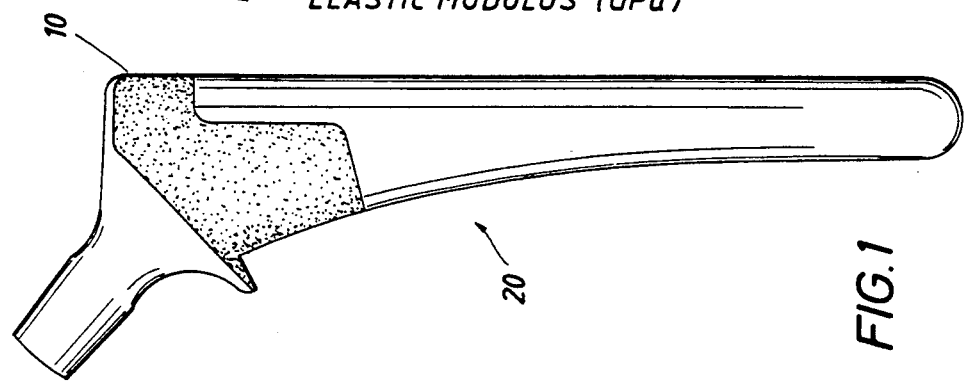
FIG. 1 is a schematic diagram of a hip joint stem with a porous coating.

A porous coating, such as a bead or wire mesh coating, as exemplified schematically in FIG. 1 as 10 on hip stem prosthesis 20, may be applied to implants of many types for a variety of applications fabricated from the inventive alloy. Such coatings are often useful to provide interstitial spaces for tissue ingrowth into the implant, which tends to stabilize the implant in the skeletal structure. Further, even though the application of such porous coatings usually requires sintering at relatively high temperatures, the properties of the alloy that might affect its usefulness as an implant material are not adversely affected.

While prostheses fabricated from the invention alloy possess a relatively high strength, the usefulness of these prostheses is not limited to load-bearing applications. Because of its corrosion resistance and non-toxicity and relatively low modulus of elasticity, the alloy can be used to fabricate many types of orthopedic implants including, but not limited to, hip joints, knee joints, cheek bones, tooth implants, skull plates, fracture plates, intramedullary rods, staples, bone screws, and other implants.

DETAILED DESCRIPTION OF THE PREFERRED EMBODIMENTS

The inventive alloy may be produced by combining, as commercially pure components, titanium, zirconium and niobium in the appropriate proportions. The methods for titanium alloy production, such as casting, powder metallurgy, etc., are well known to those of ordinary skill in the art of metallurgy and the production of the alloy requires no special skills or precautions beyond the materials, proportions and techniques described below.

The inventive alloy contains titanium as the major component comprising about 74 wt. % of the alloy in combination with about 13 wt. % of zirconium and 13 wt. % of niobium. While tantalum may be substituted for niobium to stabilize the β-phase titanium, niobium is the preferred component due to its effect of lowering the elastic modulus of the alloy when present in certain specific proportions. Other elements are not deliberately added to the alloy but may be present in such quantities that occur as impurities in the commercially pure titanium, zirconium, niobium or tantalum used to prepare the alloy and such contaminants as may arise from the melting (alloying) process. Non-toxic filler materials, such as tantalum, could also be added to reduce the β-transus (stabilize β) and improve strength as long as the relatively low modulus of elasticity (less than about 85 GPa) of the base alloy is not significantly affected.

While the as-cast or powder metallurgically prepared alloy can be used as an implant material, it can optionally be mechanically hot rolled at 825°–875° C. After cooling, it can then be reheated to about 875° C. for about 20 minutes and then quenched with water. This reheating step may be eliminated if the alloy is quenched rapidly from the hot working temperature. These hot rolling, cooling, reheating and quenching steps develop the cast alloy into a wrought material having a finer grain than the as-cast or powder metallurgically prepared alloy and renders it more suitable for use as an implant material.

The inventive alloy, in this hot rolled, reheated and quenched form, has an elastic modulus of about 60 GPa, a tensile strength of about 700 GPa and an elongation of about 25%. While such an alloy might be suitable for use in a variety of implant applications, it is desirable that alloys used in more severe load-bearing implant applications have a greater strength as well as a lower elastic modulus (less than about 85 GPa).

In the specification and claims, the term "high strength" refers to an alloy having a tensile strength above at least about 620 MPa.

The term "low modulus" as used in the specification and claims refers to a Young's modulus below about 85 GPa.

Although the hot rolled, reheated and quenched alloy is a suitable implant material, its properties can be improved by forging or cold working or an aging heat treatment or a combination of these. Aging treatment can increase the strength and hardness of the material, and reduce its elongation while maintaining a relatively low modulus of elasticity. The treatment can be varied to obtain the desired properties.

In titanium alloys, the niobium (or tantalum, if this element is added) acts to stabilize the β-phase since it is a β-isomorphous phase stabilizer. This results in a lower β-phase transus temperature and upon rapid cooling from about the β-transus temperature, the presence of a greater proportion of the β-phase titanium in the alloy microstructure. This enhances the ability of the alloy to harden on subsequent aging.

Niobium, in particular, when present in preferred quantities of from about 6 to about 10 atomic percent (most preferably about 8 atomic percent) or in an alternative preferred range of from about 22 to 32 atomic percent, produces a low modulus composition when alloyed with titanium. Deviation from these ranges of niobium concentration tends to increase the elastic modulus. In weight percent terms, these preferred compositional ranges of niobium in the titanium-zirconium alloy translate to about 10 to about 20 wt. % and about 35 to about 50 wt. %.

Titanium alloys containing about 13 wt. % niobium correspond to those having about 8 atomic percent niobium. Thus, the Ti-13Nb-13Zr alloy is believed to identify an optimal low modulus, titanium alloy composition.

As previously mentioned, tantalum may be substituted for niobium to stabilize the β-phase, but niobium is preferred due to its effect in reducing the elastic modulus. Substitution with zirconium can improve strength.

Whereas the niobium proportion is critical to obtain the desired low modulus property, the zirconium proportion is not as critical. It is desirable to maintain the proportion of zirconium at less than about 20 wt. % but higher proportions are also useful.

Zirconium, it is believed, is capable of stabilizing both α- and β-phase titanium alloy, but acts by being in solution in the alloy as a β-stabilizer by slowing the transformation process in the inventive alloy. It is further believed that the larger ionic radius of zirconium (35% larger than that of titanium) helps to disrupt ionic bonding forces in the alloy resulting in some reduction in the modulus of elasticity.

In order to effect the transition to the β-phase, the alloy may be treated by heating to about 875° C. for about 20 minutes. Lower temperatures above the β-transus may also be used. The β-phase may also be induced by heating to higher temperatures for shorter periods of time. The critical factor is heating to at least about the β-transition temperature, about 728° C for Ti-13Zr-13Nb, for a period of time sufficient to obtain a substantial conversion of the titanium alloy to the β-phase prior to cooling to room temperature. Conversion of the alloy to the β-phase and cooling may be effected before during, or after shaping for implantation and sintering of a porous metal coating, whichever is most convenient.

Figure 4A:
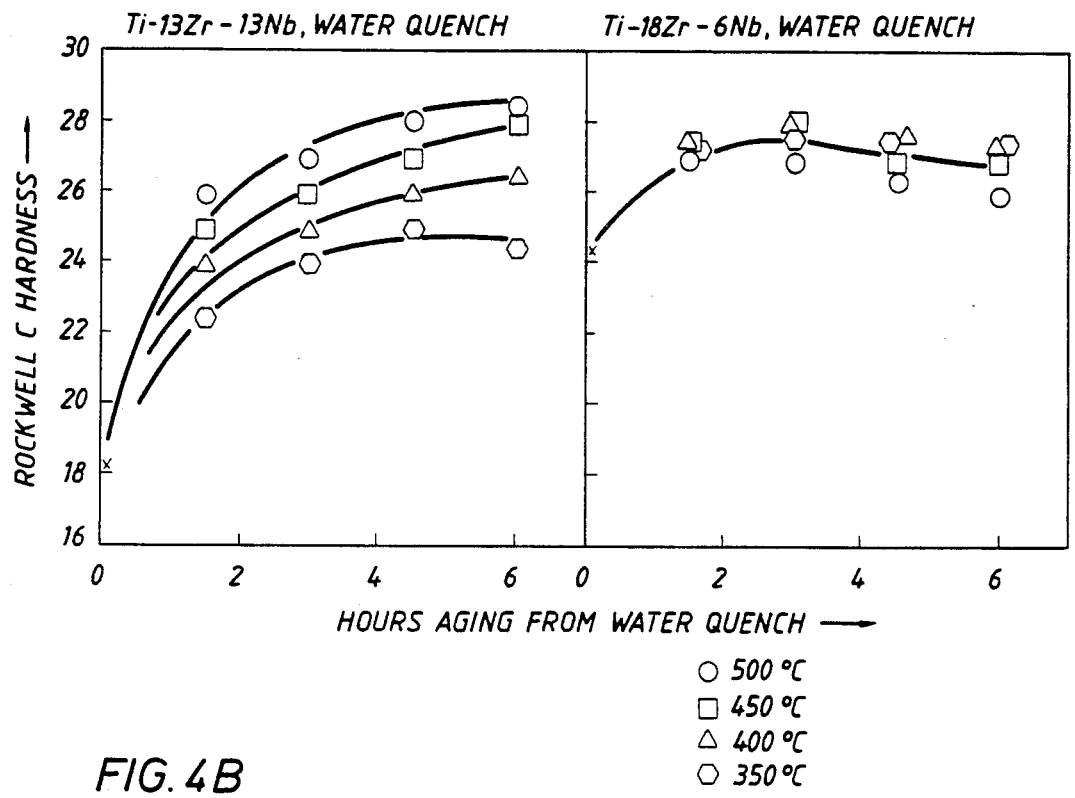
FIGS. 4a, 4b shows the effect of various techniques of age hardening on two different invention alloys.
Figure 4B:
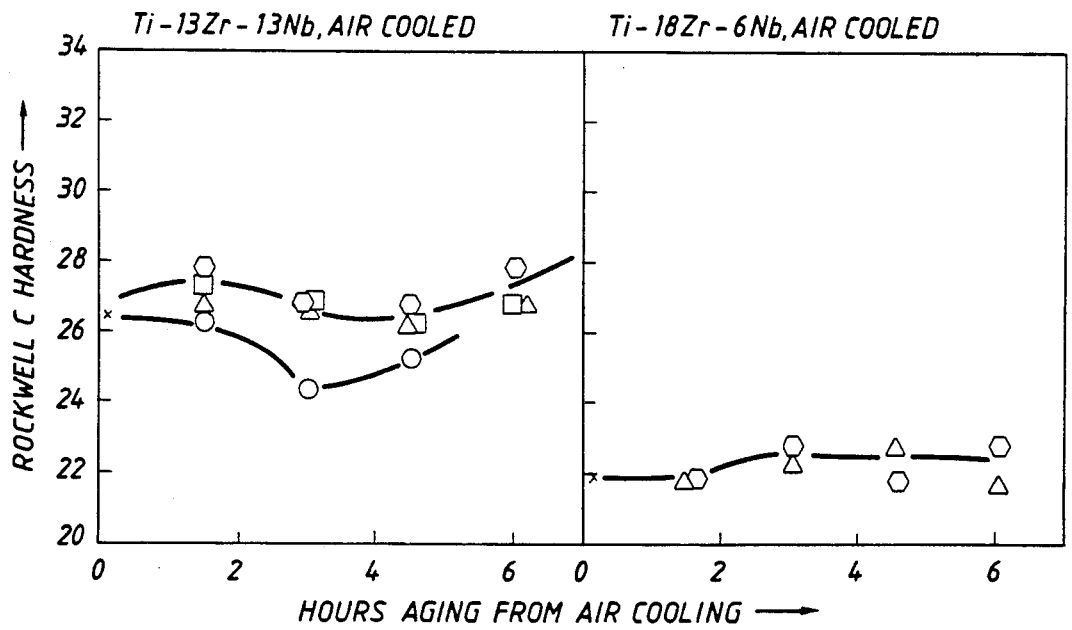

The effect of hardness and aging conditions for Ti-13Zr-13Nb and Ti-18Zr-6Nb alloys cooled at two different rates from above the beta transus are shown in FIGS. 4A and 4B. In FIG. 4A, a water quench is used whereas in FIG. 4B, air cooling is employed.

Based upon the foregoing, it is apparent that the titanium proportion of certain embodiments of the invention alloy could be less than 50 wt. %. Nevertheless, these alloys are, for purposes of the specification and claims, referred to as "titanium alloys." For example, a titanium alloy may contain 20 wt. % zirconium and 45 wt. % niobium with only 35 wt. % titanium.

The machining, casting or forging of the alloy into the desired implant shape may be carried out by any of conventional methods used for titanium alloys. Further, implants could be pressed from the powdered alloy under conditions of heat and pressure in pre-forms in the shape of the desired implant. Conventional sintering and hot isostatic pressure treatments can be applied.

While the alloy provides a non-toxic prosthesis, it may yet be desirable for other reasons such as microfretting against bone or polyethylene bearing surfaces to coat the prosthesis. In this event, the surface of the prosthesis may be coated with an amorphous diamond-like carbon coating or ceramic-like coating such as titanium nitride or titanium carbide using chemical or plasma vapor deposition techniques to provide a hard, impervious, smooth surface coating. These coatings are especially useful if the prosthesis is subjected to conditions of wear, such as, for instance, in the case of bearing surfaces of knee or hip prostheses.

Methods for providing hard, low-friction, impervious, biocompatible amorphous diamond-like carbon coatings are known in the art and are disclosed in, for example, EPO patent application 302 717 A1 to Ion Tech and Chemical Abstract 43655P, Vol. 101 describing Japan Kokai 59/851 to Sumitomo Electric, all of which are incorporated by reference herein as though fully set forth.

Implants fabricated from the inventive alloy may be supplied with a porous bead or wire coating of titanium alloy of the same or different composition including pure titanium to allow stabilization of the implant in the skeletal structure of the patient after implantation by bone ingrowth into the porous structure. Such porous structures are normally attached to the implant surface by sintering. This involves heating the implant to above about 1250° C. The mechanical properties of titanium alloys can change significantly due to substantial grain growth and other metallurgical factors arising from the sintering process. Thus, after sintering to attach the porous coating, it is preferred that the Ti-13Zr-13Nb implant be reheated to about 875° C. (or above the $\beta$-transus) for 20-40 minutes then quenched before being aged at about 500° C. for about 6 hours to restore mechanical properties. If quenched adequately from the sintering temperature, it may be possible to go directly to the aging process.

The following examples are intended to illustrate the invention as described above and claimed hereafter and are not intended to limit the scope of the invention in any way. The aging temperature used in the examples is determined to be acceptable, but not necessarily optimal, based on the hardness versus aging response show in FIGS. 4A and 4B.

EXAMPLE 1

An alloy including, by weight, 74% titanium, 13% niobium and 13% zirconium, was hot rolled at a temperature in the range 825°-875° C. to 14 mm thick plate. The plate was cooled to room temperature then reheated to 875° C. where it was maintained for 20 minutes and then water quenched to room temperature. The $\beta$-transus for this alloy was about 728° C. as compared to about 1000° C. for Ti-6Al-V. The mechanical properties of the heat-treated, quenched Ti-Zr-Nb alloy, which has an acicular transformed $\beta$-structure, are shown in Table I.

TABLE I

| Mechanical Properties of Ti—13Zr—13Nb As Water Quenched from Hot Rolling Temperature ||
| --- | --- |
| Tensile Strength | 710 MPa |
| Yield Strength | 476 MPa |
| Elongation | 26% |
| Reduction in Area | 70% |
| Young's Modulus | 62 GPa |
| Rockwell C Hardness | 18-19 |

EXAMPLE 2

The heat-treated, quenched Ti-Zr-Nb alloy of Example 1 was aged by heating at 500° C. for 6 hours. The mechanical properties of this aged alloy are shown in Table II.

TABLE II

| Mechanical Properties of Quenched Ti—13Zr—13Nb Aged 500° C. for Six Hours ||
| --- | --- |
| Tensile Strength | 917 MPa |
| Yield Strength | 796 MPa |
| Elongation | 13% |
| Reduction in Area | 42% |
| Young's Modulus | 76.6 GPa |
| Rockwell C Hardness | About 29 |

EXAMPLE 3

Samples of the alloy of Example 1 were sintered at about 1250° C. to attach a porous titanium bead coating of the type shown in FIG. 1. The bead-coated alloy samples were then reheated to 875° C. and maintained at this temperature for 40 minutes before being water-quenched. A group of six samples were aged at 500° C. for 6 hours and the mechanical properties of aged and non-aged samples (three each) were tested and are shown in Table III.

TABLE III

| Mechanical Properties of Ti—13Zr—13Nb Alloy Following Bead Sintering, Reheating to 875° C., and Water Quenched |||
| --- | --- | --- |
| | As-Quenched (Avg.) | Aged (500° C. Six Hours) |
| Tensile Strength | 664 MPa | 900 MPa |
| Yield Strength | 465 MPa | 795 MPa |
| Elongation | 20% | 4% |
| Reduction Area | 46% | 9% |
| Young's Modulus | 61.8 GPa | 74.7 GPa |

Note that the sintering treatment can significantly alter the mechanical properties, particularly ductility. Thus, an alloy acceptable for a particular application in unsintered form may not necessarily be effective in that application following a high-temperature sintering treatment routinely used to attach a porous titanium coating. To minimize these effects, lower temperature diffusion bonding methods can be used in which a sintering temperature near the $\beta$-transus may be effective. Alternatively, pre-sintered porous metal pads can be tack-welded to the implant.

EXAMPLE 4

A comparison of the elastic modulus, tensile strength and yield strength of the Ti-13Zr-13Nb invention alloy with those of known alloys, composites and cortical bone, are summarized in FIGS. 2 and 3. $Al_2O_3$ and $ZrO_2$ refer to ceramics while C/PEEK refers to a carbon reinforced polyetheretherketone composite and C/PS refers to a carbon reinforced polysulfone composite. All the mechanical property data of FIGS. 2 and 3 were obtained from literature sources except for the data pertaining to the invention alloy which were measured using standard ASTM tensile testing techniques. It is significant that the Ti-13Zr-13Nb invention alloy has an elastic modulus similar to carbon fiber reinforced composites and closer to that of bone than the other metals (FIG. 2) while at the same time possessing a strength comparable to or better than other metals (FIG. 3).

EXAMPLE 5

A sample of Ti-18Zr-6Nb was sintered to attach a porous metal coating. Thereafter, the sintered alloy was reheated to 875° C., i.e. above the $\beta$-transus, and water quenched. The properties of the as-quenched alloy are shown in Table IV. The sample was then aged at 450° C. for 3 hours and tested. These results are also shown in Table IV.

As compared to the Ti-13Zr-13Nb alloy of Example 3, this alloy's modulus of elasticity is not as low but is still lower than that of Ti-6Al-4V. Further, the Ti-18Zr-6Nb alloy has a relatively low β-transus, about 760° C. compared to that of Ti-6Al-4V which is about 1000° C.

TABLE IV

Mechanical Properties of Ti—18Zr—6Nb Following A High Temperature Sintering Treatment, Reheating to 875° C., and Water Quenching and Aging

|  | As-Quenched | Aged 450° C., 3 Hrs. |
| --- | --- | --- |
| Tensile Strength | 807 MPa | 876 MPa |
| Yield Strength | 659 MPa | 733 MPa |
| Elongation | 8% | 8% |
| Reduction in Area | 26% | 28% |
| Elastic Modulus | 85.2 GPa | 86.8% |

Note that because of the less than optimum niobium content, the elastic modulus is not as low as the previous example. Thus, proper selection of niobium content is important for optimizing the low elastic modulus. However, the presence of zirconium helps to keep the elastic modulus at an acceptably low level (less than about 85 GPa).

EXAMPLE 6

The effect of aging conditions on Ti-13Zr-13Nb and Ti-18Zr-6Nb was investigated. Separate samples of each alloy were air-cooled or water-quenched from above the β-transus, aged at 500°, 450°, 400° and 350° C. for up to 6 hours then air cooled. The results are recorded in FIG. 4.

The invention has been described with reference to its preferred embodiments. From this description, a person of ordinary skill in the art may appreciate changes that could be made in the invention which do not depart from the scope and spirit of the invention as described above and claimed hereafter.

What is claimed is:

1. In a human body wherein orthopedic implants remain for a prolonged period of time and must maintain strength and flexibility while being subjected to sustained corrosive effects of body fluids resulting in release of toxic or potentially toxic ions into surrounding tissue, the improvement wherein the implant has the alloy composition comprising: from about 10 to about 20 wt. % niobium or from about 35 to about 50 wt. % niobium; from about 13 to about 20 wt. % zirconium; and the balance titanium;

said alloy composition excluding metal ions harmful to the human body and having a modulus of elasticity of less than 85 GPa.

2. The improved implant of claim 1 wherein the alloy forming the implant has an elastic modulus of from about 60 to about 85 GPa.

3. The improved implant of claim 1 consisting essentially of about 74 wt. % titanium, about 13 wt. % niobium, and about 13 wt. % zirconium.

4. The improved implants of claim 1 wherein the alloy composition includes an amount of tantalum as a β-stabilizer sufficient to stabilize a β-phase in the alloy composition of the implant without significantly affecting the modulus of elasticity of the implant.

5. The improved implants of claims 2 or 3 further comprising at least a partial outer surface coating comprising the oxides, carbides or nitrides of the elements selected from the group consisting of titanium, niobium and zirconium.

6. The improved implants of claims 2 or 3 further comprising at least a partial outer surface coating of amorphous diamond-like carbon.

7. The improved implants of claims 2 or 3 further comprising a surface coating of porous beads or wire mesh for the ingrowth of tissue into the surface coating to stabilize the implant in the body environment.

* * * * *